US009421202B2

(12) United States Patent
Hergenrother et al.

(10) Patent No.: US 9,421,202 B2
(45) Date of Patent: Aug. 23, 2016

(54) PROCASPASE COMBINATION THERAPY FOR GLIOBLASTOMA

(71) Applicants: Paul J. Hergenrother, Champaign, IL (US); Rachel C. Botham, Champaign, IL (US); Timothy M. Fan, Mahomet, IL (US); Mark J. Gilbert, Seattle, WA (US); Michael J. Handley, Windsor, CO (US); Avadhut Joshi, Towson, MD (US); Gregory J. Riggins, White Hall, MD (US); Theodore M. Tarasow, San Ramon, CA (US)

(72) Inventors: Paul J. Hergenrother, Champaign, IL (US); Rachel C. Botham, Champaign, IL (US); Timothy M. Fan, Mahomet, IL (US); Mark J. Gilbert, Seattle, WA (US); Michael J. Handley, Windsor, CO (US); Avadhut Joshi, Towson, MD (US); Gregory J. Riggins, White Hall, MD (US); Theodore M. Tarasow, San Ramon, CA (US)

(73) Assignees: The Board of Trustees of the University of Illinois, Urbana, IL (US); Vanquish Oncology, Inc., Champaign, IL (US); The Johns Hopkins University, Baltimore, MD (US)

( * ) Notice: Subject to any disclaimer, the term of this patent is extended or adjusted under 35 U.S.C. 154(b) by 0 days.

(21) Appl. No.: 14/383,460

(22) PCT Filed: Mar. 6, 2013

(86) PCT No.: PCT/US2013/029391
§ 371 (c)(1),
(2) Date: Sep. 5, 2014

(87) PCT Pub. No.: WO2013/134398
PCT Pub. Date: Sep. 12, 2013

(65) Prior Publication Data
US 2015/0025083 A1 Jan. 22, 2015

Related U.S. Application Data

(60) Provisional application No. 61/607,103, filed on Mar. 6, 2012.

(51) Int. Cl.
*A61K 31/497* (2006.01)
*A61K 31/495* (2006.01)
*A61K 31/4188* (2006.01)
*A61K 9/00* (2006.01)
*A61K 47/10* (2006.01)
*A61K 9/20* (2006.01)
*A61K 9/48* (2006.01)

(52) U.S. Cl.
CPC ............... *A61K 31/495* (2013.01); *A61K 9/008* (2013.01); *A61K 9/0019* (2013.01); *A61K 9/2018* (2013.01); *A61K 9/2054* (2013.01); *A61K 9/4858* (2013.01); *A61K 31/4188* (2013.01); *A61K 47/10* (2013.01)

(58) Field of Classification Search
CPC ............ A61K 2300/00; A61K 31/495; A61K 31/4188; A61K 47/10; A61K 9/0019; A61K 9/008; A61K 9/2018; A61K 9/2054; A61K 9/4858
See application file for complete search history.

(56) References Cited

U.S. PATENT DOCUMENTS

| | | | |
|---|---|---|---|
| 6,303,329 B1 | 10/2001 | Heinrikson et al. | |
| 6,403,765 B1 | 6/2002 | Alnemri | |
| 6,534,267 B1 | 3/2003 | Wang et al. | |
| 6,762,045 B2 | 7/2004 | Krebs et al. | |
| 6,878,743 B2 | 4/2005 | Choong et al. | |
| 7,041,784 B2 | 5/2006 | Wang et al. | |
| 7,632,972 B2 | 12/2009 | Hergenrother et al. | |
| 8,592,584 B2 | 11/2013 | Hergenrother et al. | |
| 2004/0180828 A1 | 9/2004 | Shi | |
| 2007/0049602 A1* | 3/2007 | Hergenrother et al. | 514/252.12 |
| 2010/0291214 A1 | 11/2010 | Gabriele et al. | |
| 2011/0257398 A1 | 10/2011 | Hergenrother et al. | |
| 2012/0040995 A1 | 2/2012 | Hergenrother et al. | |
| 2012/0178803 A1* | 7/2012 | Harn et al. | 514/473 |

FOREIGN PATENT DOCUMENTS

| | | |
|---|---|---|
| RU | 2410389 C2 | 9/2006 |
| RU | 2439695 C2 | 11/2006 |
| RU | 2360692 C1 | 12/2007 |
| RU | 2408584 C2 | 1/2011 |
| WO | 2008134474 A2 | 11/2008 |
| WO | 2009089508 A1 | 7/2009 |

OTHER PUBLICATIONS

Temozoloamide product specification, Oct. 5, 2006.*
Rasheed et al, Sci Pharm. 2008; 76: 567-598.*
Peterson et al., "Discovery and Canine Preclinical Assessment of a Nontoxic Procaspase-3-Activating Compound," Cancer Research, Sep. 15, 2010. 70: pp. 7232-7241.
Peterson et al., "PAC-1 Activates Procaspase-3 in Vitro through Relief of Zinc-Mediated Inhibition," J. Mol. Biol., Mar. 10, 2009. 388: pp. 144-158.

(Continued)

*Primary Examiner* — Jean Cornet
(74) *Attorney, Agent, or Firm* — Haukaas Fortius PLLC; Michael H. Haukaas

(57) ABSTRACT

The invention provides compositions and methods for the induction of cell death, for example, cancer cell death. Combinations of compounds and related methods of use are disclosed, including the use of compounds in therapy for the treatment of cancer and selective induction of apoptosis in cells. The disclosed drug combinations can have lower neurotoxicity effects than other compounds and combinations of compounds.

20 Claims, 4 Drawing Sheets

(56) References Cited

OTHER PUBLICATIONS

Peterson et al., "Procaspase-3 Activation as an Anti-Cancer Strategy: Structure-Activity Relationship of Procaspase-Activating Compound 1 (PAC-1) and Its Cellular Co-Localization with Caspase-3," J. Med. Chem., Aug. 8, 2009. 59: pp. 5721-5731.

Putt et al., "Small-molecule activation of procaspase-3 to caspase-3 as a personalized anticancer strategy," Nat Chem. Biol., Oct. 2006. 2: pp. 543-550.

Wolan et al., "Small-Molecule Activators of a Proenzyme," Science Mag, 2009. 326: pp. 852-858.

Zorn et al., "Self-Assembling Small Molecules Form Nanofibrils That Bind Procaspase-3 to Promote Activatoin," J. of the American Chem. Soc., Nov. 8, 2011., 133: pp. 19630-19633.

International Search Report and Written Opinion for PCT/US2013/029391, dated Mar. 6, 2013, 2 pp.

International Preliminary Report on Patentability for PCT/US2013/029391, dated Sep. 18, 2014, 5 pp.

* cited by examiner

PAC-1 synergizes with TMZ to extend survival in a mouse model of metastatic osteosarcoma

Control
Day 18

PAC-1 + TMZ
Day 53

PROCASPASE COMBINATION THERAPY FOR GLIOBLASTOMA

RELATED APPLICATIONS

This application claims priority under 35 U.S.C. §119(e) to U.S. Provisional Patent Application No. 61/607,103, filed Mar. 6, 2012, which is incorporated herein by reference.

BACKGROUND OF THE INVENTION

Apoptosis, or programmed cell death, plays a central role in the development and homeostasis of all multicellular organisms. A frequent hallmark of cancer is resistance to natural apoptotic signals. Depending on the cancer type, this resistance is typically due to up- or down-regulation of key proteins in the apoptotic cascade or to mutations in genes encoding these proteins. Such changes occur in both the intrinsic apoptotic pathway, which funnels through the mitochondria and caspase-9, and the extrinsic apoptotic pathway, which involves the action of death receptors and caspase-8. For example, alterations in proper levels of proteins such as p53, Bim, Bax, Apaf-1, FLIP and many others have been observed in cancers. The alterations can lead to a defective apoptotic cascade, one in which the upstream pro-apoptotic signal is not adequately transmitted to activate the executioner caspases, caspase-3 and caspase-7.

As most apoptotic pathways ultimately involve the activation of procaspase-3, upstream genetic abnormalities are effectively "breaks" in the apoptotic circuitry, and as a result such cells proliferate atypically. Given the central role of apoptosis in cancer, efforts have been made to develop therapeutics that target specific proteins in the apoptotic cascade. For instance, peptidic or small molecule binders to cascade members such as p53 and proteins in the Bcl family or to the inhibitor of apoptosis (IAP) family of proteins have pro-apoptotic activity, as do compounds that promote the oligomerization of Apaf-1. However, because such compounds target early (or intermediate to high) positions on the apoptotic cascade, cancers with mutations affecting proteins downstream of those members can still be resistant to the possible beneficial effects of those compounds.

It would be advantageous for therapeutic purposes to identify small molecules that directly activate a proapoptotic protein far downstream in the apoptotic cascade. This approach could involve a relatively low position in the cascade, thus enabling the killing of even those cells that have mutations that affect upstream apoptotic machinery. Moreover, such therapeutic strategies would have a higher likelihood of success if that proapoptotic protein were upregulated or present at increased levels in cancer cells. Thus, the identity of small molecules that target the downstream effector protein of apoptosis, procaspase-3, would significantly aid current cancer therapy.

The conversion or activation of procaspase-3 to caspase-3 results in the generation of the active "executioner" caspase form that subsequently catalyzes the hydrolysis of a multitude of protein substrates. Active caspase-3 is a homodimer of heterodimers and is produced by proteolysis of procaspase-3. In vivo, this proteolytic activation typically occurs through the action of caspase-8 or caspase-9. To ensure that the zymogen (proenzyme) is not prematurely activated, procaspase-3 has a 12 amino acid "safety catch" that blocks access to the ETD site (amino acid sequence, ile-glu-thr-asp) of proteolysis. This safety catch enables procaspase-3 to resist autocatalytic activation and proteolysis by caspase-9. Mutagenic studies indicate that three consecutive aspartic acid residues appear to be the critical components of the safety catch. The position of the safety catch is sensitive to pH, thus upon cellular acidification (as occurs during apoptosis) the safety catch is thought to allow access to the site of proteolysis, and active caspase-3 can be produced either by the action of caspase-9 or through an autoactivation mechanism.

In certain cancers, the levels of procaspase-3 are elevated relative to normal tissue. A study of primary isolates from 20 colon cancer patients revealed that on average, procaspase-3 was upregulated six-fold in such isolates relative to adjacent non-cancerous tissue. In addition, procaspase-3 is upregulated in certain neuroblastomas, lymphomas, and liver cancers. Furthermore, a systematic evaluation was performed of procaspase-3 levels in the 60 cell-line panel used for cancer screening by the National Cancer Institute (NCI) Developmental Therapeutics Program, which revealed that certain lung, melanoma, renal, and breast cancers show greatly enhanced levels of procaspase-3 expression.

Due to the role of active caspase-3 in achieving apoptosis, the relatively high levels of procaspase-3 in certain cancerous cell types, and the intriguing safety catch-mediated suppression of its autoactivation, small molecules that directly modify procaspase-3 could have great applicability in targeted cancer therapy.

Combination therapy has become standard for treatment of cancer patients. The goal of combination therapy drug cocktail regimes is to achieve a synergistic or additive effect between chemotherapeutics, thereby facilitating shortened treatment times, decreased toxicity, and increased patient survival. Drugs that act on a single biochemical pathway are particularly strong candidates for synergy or potentiation as they may mimic "synthetic lethal" genetic combinations. For example, inhibitors of poly(ADP-ribose)polymerase-1 (PARP-1), an enzyme that facilitates DNA damage repair, potently synergize with DNA damaging agents as demonstrated in cell culture, animal models, and human clinical trials. However, there is still a need for more effective therapies for the treatment of many forms of cancer, and new synergistic combinations of anticancer drugs would aid this pursuit. Accordingly, there exists a need to identify new cytotoxic agents that are effective in killing cancer cells yet protect normal host tissues from the undesired toxicity of the cytotoxic agent.

SUMMARY

The invention broadly provides compounds, compositions, and methods of therapeutic treatment. In various embodiments, the inventions are applicable to a variety of cancer diseases and cancer cell types such as breast, lymphoma, adrenal, renal, melanoma, leukemia, neuroblastoma, lung, brain, and others known in the art. Herein is disclosed, inter alia, compositions and methods including small molecules capable of inducing cell death. In some embodiments, the compositions and methods involve compounds that can interact directly or indirectly with programmed cell death pathway members such as procaspase-3. In certain embodiments, the compositions and methods have reduced neurotoxicity compared to other compounds that interact directly or indirectly with programmed cell death pathway members such as procaspase-3.

Combination anticancer therapy can consist of drugs that target different biochemical pathways, or those that hit different targets in the same pathway, mimicking "synthetic lethal" genetic combinations. The combination of the procaspase-3 activator PAC-1 and the alkylating agent temozolomide (TMZ) shows considerable synergy toward inducing apoptotic death of cancer cells to a degree well exceeding the additive effect. The combination of PAC-1 and TMZ effectively reduces tumor burden in tumor models in which the compounds alone have minimal or no effect. These data indicate the efficacy of PAC-1/TMZ combination for the treatment of cancer and, more broadly, show that this synergistic combination can provide significantly heightened therapeutic benefits.

Accordingly, the invention provides a composition comprising (a) a compound of Formula (I):

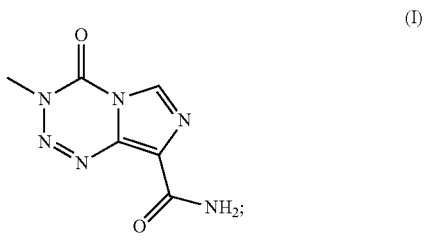

(b) the compound PAC-1:

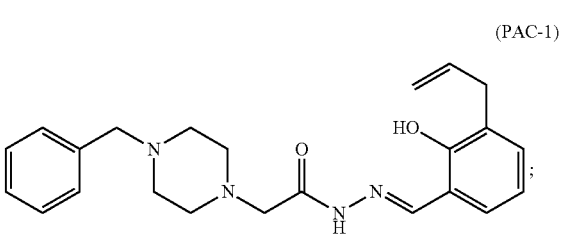 [SMILES: C=CCc1cccc(/C=N/NC(=O)CN2CCN(Cc3ccccc3)CC2)c1O]

and (c) a pharmaceutically acceptable diluent, excipient, or carrier. The compound of Formula (I) can be temozolomide (TMZ). In other embodiments, the structure of the compound of Formula (I) can be replaced with a derivative of TMZ, or a prodrug thereof. The carrier can include water and optional components for advantageously delivering the actives such as a buffer, a sugar, a cyclodextrin, or various combinations thereof. In one embodiment, the cyclodextrin is 2-hydroxypropyl-β-cyclodextrin.

The concentration of the compound of Formula I can be about 100 µM to about 1 mM, typically about 250 µM, about 500 µM, or about 750 µM. The concentration of PAC-1 can be about 2 µM to about 50 µM, typically about 2.5 µM, about 5 µM, about 7.5 µM, about 10 µM, about 12.5 µM, about 15 µM, about 20 µM, about 25 µM, about 30 µM, about 40 µM, or about 50 µM. For example, in one embodiment the concentration of the compound of Formula I can be about 250 µM to about 750 µM and the concentration of PAC-1 can be about 5 µM to about 30 µM.

The invention also provides a method of inhibiting the growth or proliferation of cancer cells. The method includes contacting cancer cells with an effective amount of a composition of described herein, wherein the composition can include one or both of PAC-1 and TMZ. When the composition includes only one of PAC-1 and TMZ, the method includes subsequently contacting the cancer cells with the other. Contacting the cancer cells with these actives (PAC-1 and TMZ) inhibits the growth or proliferation of the cancer cells.

The invention further provides a method of inducing apoptosis in a cancer cell comprising contacting the cancer cell with an effective amount of a compound of Formula (I):

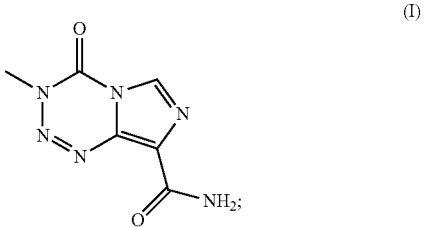

and an effective amount of the compound PAC-1:

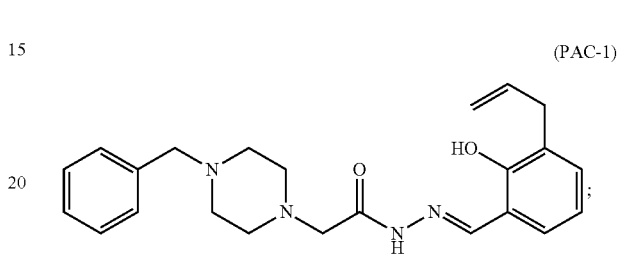

wherein apoptosis is thereby induced in the cancer cell. The contacting can be in vitro. Alternatively, the contacting can be in vivo. In one embodiment, the cancer cell can be contacted with the compound of Formula (I) and PAC-1 concurrently. In another embodiment, the cancer cell can be contacted with the compound of Formula (I) prior to contacting the cancer cell with PAC-1. In yet another embodiment, the cancer cell can be contacted with PAC-1 prior to contacting the cancer cell with the compound of Formula (I).

The invention also provides a method of treating a cancer in a patient in need thereof. The method includes administering to a patient, concurrently or sequentially, a therapeutically effective amount of a compound of Formula (I):

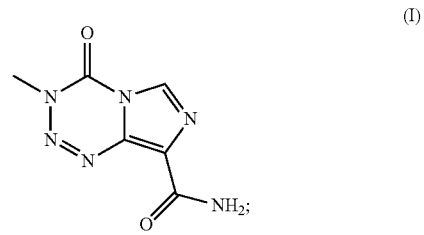

and an effective amount of the compound PAC-1:

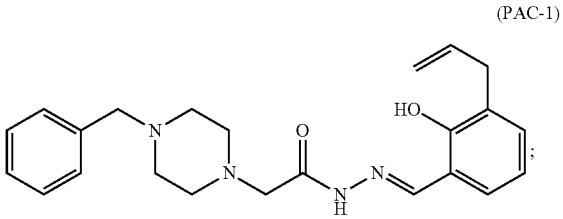 [SMILES: C=CCc1cccc(/C=N/NC(=O)CN2CCN(Cc3ccccc3)CC2)c1O]

wherein the cancer is thereby treated. In one embodiment, the compound of Formula (I) and the compound PAC-1 can be administered concurrently. In another embodiment, the compound of Formula (I) and the compound PAC-1 are administered sequentially. When administered sequentially, the compound of Formula (I) can be administered before the compound PAC-1, or the compound of Formula (I) can be administered after the compound PAC-1.

The cancer cells of various embodiments can be cancer cells in brain tissue, or cancer cells in bone tissue. For example, the cancer cells can be glioblastoma cells or oligodendroglioma cells. In another embodiment, cancer cells can be osteosarcoma cells. Other types of cancer cells that can be inhibited and cancerous conditions that can be treated are further described below.

The invention thus provides for the use of the compositions described herein for use in medical therapy. The medical therapy can be treating cancer, for example, breast cancer, lung cancer, pancreatic cancer, prostate cancer, colon cancer, and other cancers recited herein. The invention also provides for the use of a composition as described herein for the manufacture of a medicament to treat a disease in a mammal, for example, cancer in a human. The invention thus provides for the use of the compounds described herein for the manufacture of medicaments useful for the treatment of cancer in a mammal, such as a human. The medicament can include a pharmaceutically acceptable diluent, excipient, or carrier.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

DETAILED DESCRIPTION

Figure 1:
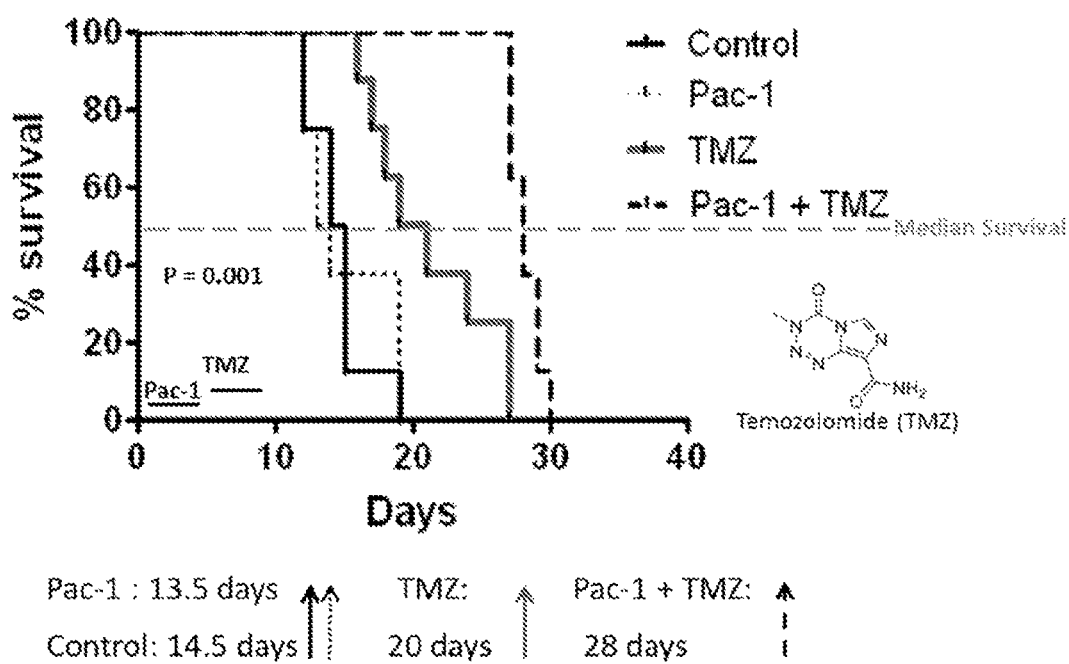
FIG. 1. PAC-1 synergizes with TMZ to extend survival in a rat model of glioblastoma: Survival graph of the four 9 L intercranial syngeneic rat model groups. 9 L (rat glioma) cells were intracranially implanted in rats. PAC-1 (50 mg/kg in water) was administered via oral gavage on days 0-4, and TMZ (50 mg/kg in water) was given via oral gavage on days 5-9; 8 rates per group. P-value is relative to TMZ alone. Median survival times: Control, 14.5 days; PAC-1, 13.5 days; TMZ, 20 days; Combo, 28 days. Overall p value of the combo curve is p=0.0001. TMZ alone to Combo, p=0.0007 (log rank test) and p=0.001 (Gehan-Breslow-Wilcoxon test).

As a further introduction, compounds capable of activating an enzyme that is often overexpressed or otherwise present at increased levels in its inactive form in cancer cells have been discovered. The compounds can induce programmed cell death (apoptosis) in cancer cells, including those that have upregulated or increase levels of procaspase-3. Many cancers resist standard chemotherapy. The combination therapy described herein takes advantage of the procaspase-1 activation by PAC-1, which synergizes with the DNA alkylation properties of TMZ, to provide efficacy under conditions where one of the actives alone would be less effective or completely ineffective. These compounds can also be successful in targeted cancer therapy, where there can be advantages of selectivity in the killing of cancer cells with comparably reduced adverse reactions to non-cancerous cells having lower levels of procaspase-3. These adverse reactions can include toxicity, particularly neurotoxicity.

The combination of compounds, compositions and methods described herein can act via modulation of apoptosis or programmed cell death and DNA alkylation to be effective in the treatment of cancer cells. In one embodiment, the modulation of apoptosis is by induction or activation of apoptosis. In various embodiments, the administration of compounds can be concurrent, or alternatively, sequential.

The invention thus provides methods for potentiation of temozolomide (TMZ) by PAC-1, for example, for the treatment of glioblastoma or osteosarcoma. During apoptosis, the zymogen procaspase-3 is activated via proteolysis to caspase-3, and this active caspase-3 then cleaves scores of cellular substrates, executing the apoptotic program. Because procaspase-3 protein levels are elevated in various tumor histologies, drug-mediated direct activation of procaspase-3 can be highly effective as a selective anticancer strategy.

Certain compounds can enhance the activity and automaturation of procaspase-3 and induce apoptosis in cancer cells. Procaspase-activating compound-1 (PAC-1) enhances the activity of procaspase-3 via the chelation of inhibitory zinc ions, induces apoptosis in cancer cells in culture, and has efficacy in multiple murine tumor models. A novel combination of therapeutic agents, PAC-1 and TMZ, has been found to be synergistically effective in treating cancer cells, particularly glioblastoma cells and osteosarcoma cells.

Model experiments in the 9 L rat glioblastoma cell line provide clear data to support the findings of synergy and efficacious activity of the drug combination. The in vivo rat experiments employed 9 L cells, a very aggressive tumor model, implanted inter-cranially in rats in 3 treatment groups (PAC-1 alone, TMZ alone, and the combination of PAC-1 and TMZ) and one control group.

PAC-1 was suspended in water, and given to the rats via oral gavage at 50 mg/kg (a relatively low dose) for 5 days followed by five days of TMZ dosing. No neurotoxicity was observed with PAC-1 in mice when the compound is given orally at up to 200 mg/kg, and no neurotoxicity was observed in the instant experiments. The survival benefit for the rats treated with the combination was significant and unusually dramatic (FIG. 1).

FIG. 1 schematically illustrates the data obtained when 9 L cells were intracranially implanted in rats. PAC-1 (50 mg/kg in water) was administered via oral gavage on days 0-4, and TMZ (50 mg/kg in $H_2O$) was given via oral gavage on days 5-9. Eight rats per group; a p-value of 0.001 was obtained, relative to TMZ alone (Gehan-Breslow-Wilcoxon test).

The initial assessment for the $IC_{50}$ for PAC-1 with the 9 L cell line is about 7 μM (72 hour experiment). The 9 L cell line brain tumors are typically hemorrhagic, but in the PAC-1/TMZ treated rats, the tumors were not hemorrhagic, indicating an anti-angiogenic effect.

Figure 2A:
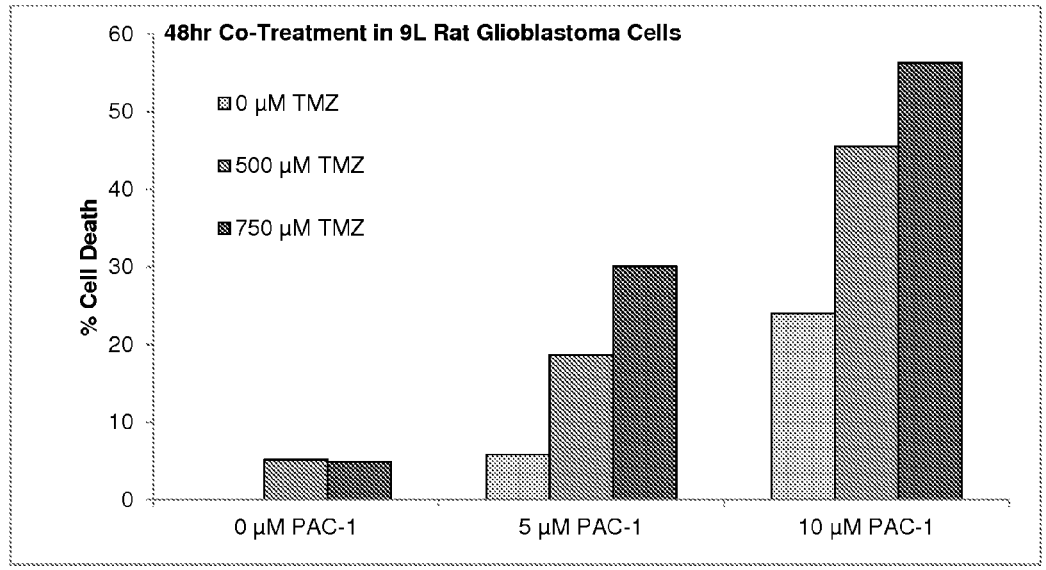
FIG. 2. PAC-1 synergizes with TMZ to induce death of glioblastoma cells in culture. A) 9 L glioblastoma cells were exposed to the indicated concentrations of PAC-1+TMZ, and cell death was assessed at 48 hours (no detectable cell death at 0 μM TMZ with 0 μM PAC-1). B) D-54 human glioblastoma cells were exposed to the indicated concentrations of PAC-1+TMZ, and cell death was assessed at 24 hours (no detectable cell death at 0 μM TMZ with 0 μM PAC-1). Dotted horizontal lines indicate cell death levels expected from a mere additive effect of compounds. The legends correspond to the bars of the bar graph where the top legend entry corresponds to the left-most bar, and the remaining legend entries correspond to the remaining bars, top to bottom corresponding to left to right, respectively.
Figure 2B:
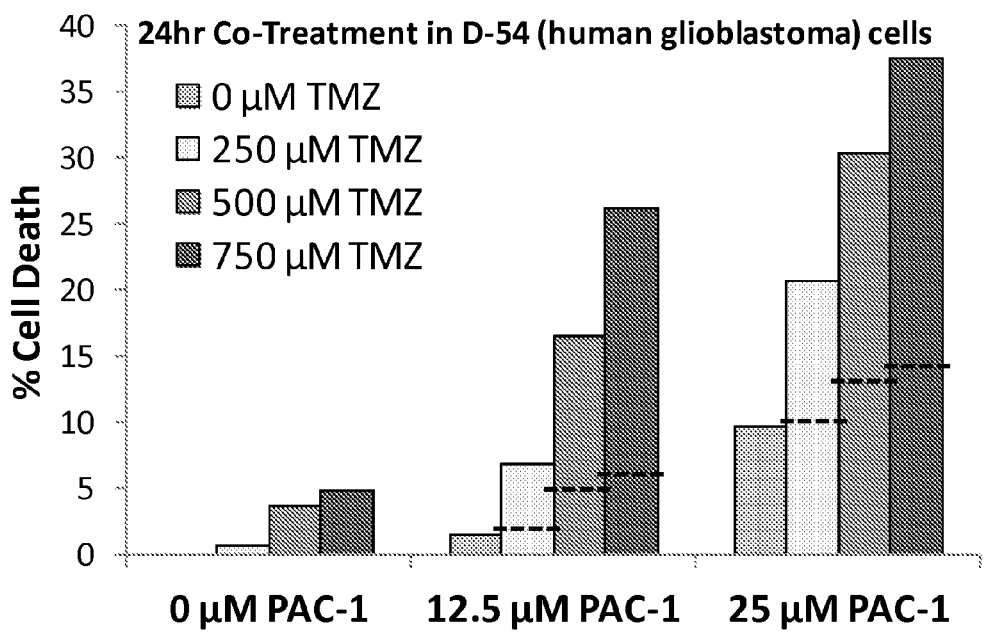
Figure 3A:
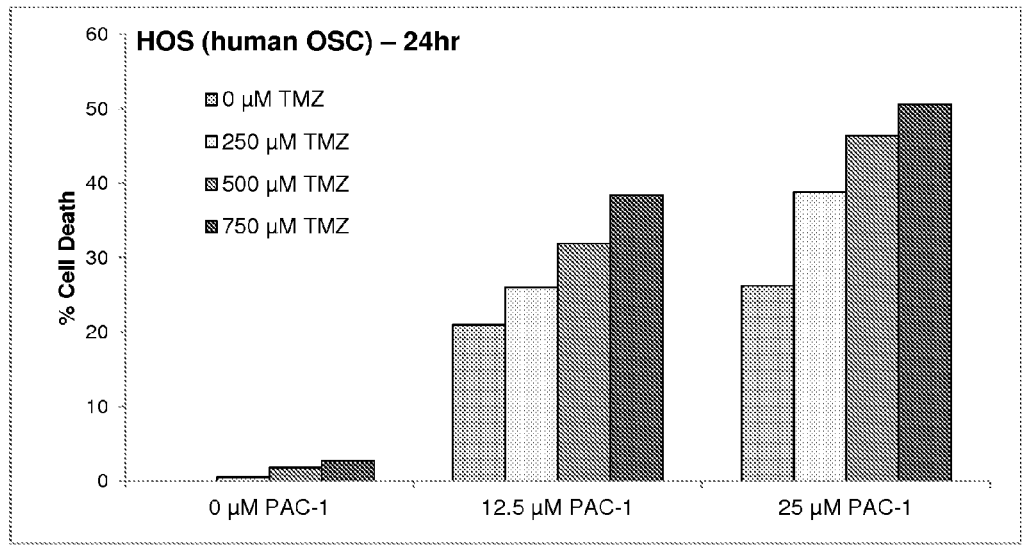
FIG. 3. PAC-1 synergizes with TMZ to induce death of osteosarcoma cells in culture. A) HOS cells were exposed to the indicated concentrations of PAC-1+TMZ and cell death was evaluated at 24 hours (no detectable cell death at 0 μM TMZ with 0 μM PAC-1). B) 143B cells were exposed to the indicated concentrations of PAC-1+TMZ and cell death was evaluated at 24 hours (no detectable cell death at 0 μM TMZ or 250 μM TMZ with 0 μM PAC-1). The legends correspond to the bars of the bar graph where the top legend entry corresponds to the left-most bar, and the remaining legend entries correspond to the remaining bars, top to bottom corresponding to left to right, respectively.
Figure 3B:
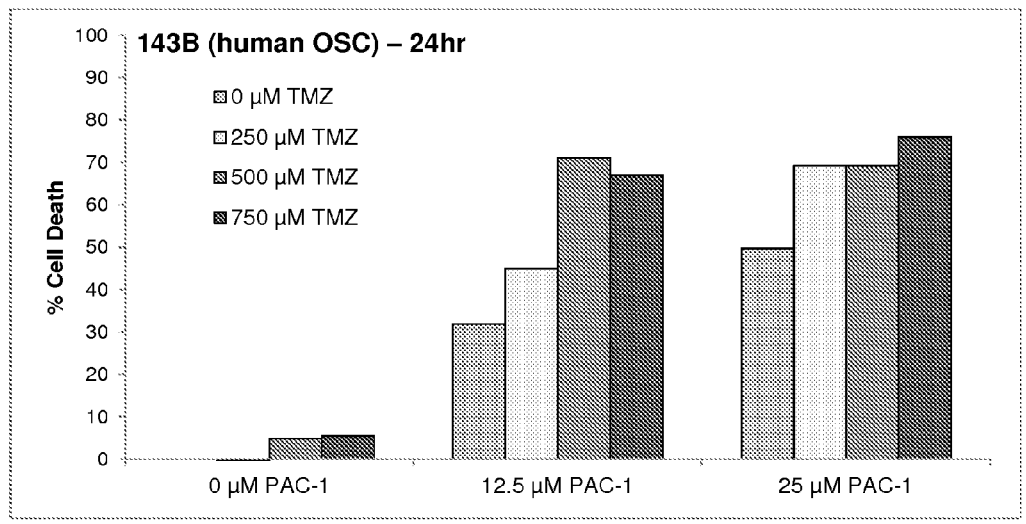
Figure 4:
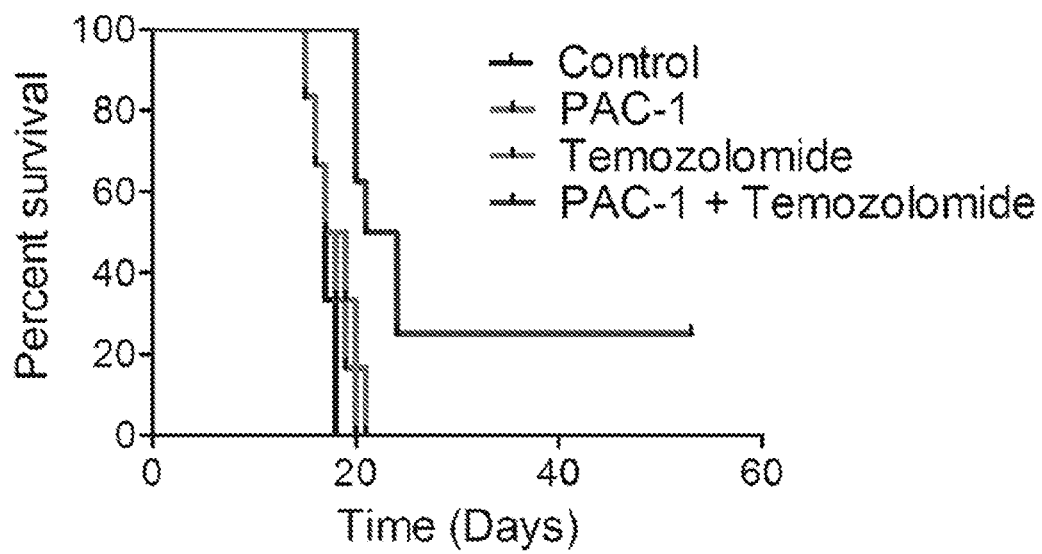
FIG. 4. PAC-1 synergizes with TMZ to extend survival in a mouse model of metastatic osteosarcoma. Seven days after injection of K7M2 cells, mice were treated orally with PAC-1 (100 mg/kg in HPβCD), TMZ (50 mg/kg oral sweet), or a sequential treatment with each, daily for five consecutive days; n=8 mice per group.
Figure 4:
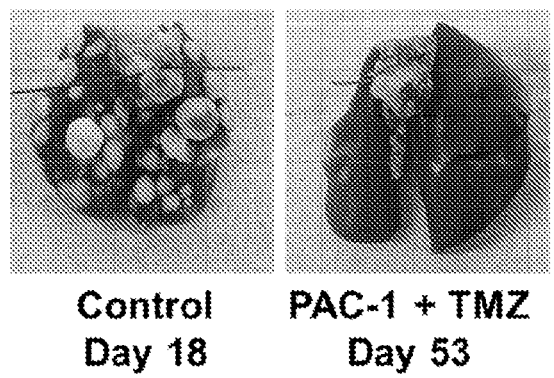

FIG. 2 shows three examples of PAC-1 synergizing with TMZ to induce the death of glioblastoma cells in culture. FIG. 3 shows two examples of PAC-1 synergizing with TMZ to induce the death of osteosarcoma cells in culture. FIG. 4 shows an example of PAC-1 synergizing with TMZ to extend survival in a mouse model of metastatic osteosarcoma.

An MTD for the PAC-1/TMZ combination is being established, and longer treatment periods (10 days each drug concurrently) and sequential and concurrent administration regimen are being evaluated. Survival benefit is being evaluated as the measurement of procaspase 3 and caspase 3 levels pre- and post-treatment. The combination therapy can also be effective for treating neurosphere cell lines derived from Hopkins glioblastoma patients, for example, in xenograft models and mammalian subjects.

Therapeutic Agents and Activity

PAC-1 (2-(4-benzylpiperazin-1-yl)-N-R2-hydroxy-3-prop-2-enyl-phenyl)methylideneaminolacetamide) selectively induces apoptosis in cancerous cells. Methods of preparing PAC-1 are described in U.S. Patent Publication No. 2012/0040995 (Hergenrother et al.).

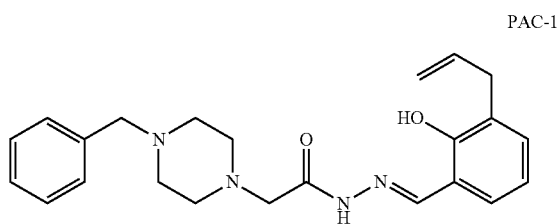 [SMILES: C=CCc1cccc(/C=N/NC(=O)CN2CCN(Cc3ccccc3)CC2)c1O]

PAC-1

Temozolomide (TMZ) is cytotoxic chemotherapy drug classified as an alkylating agent. TMZ is a derivative of imidazotetrazine, and is the prodrug of MTIC (3-methyl-(triazen-1-yl)imidazole-4-carboxamide). The preparation of TMZ and its derivatives is described in U.S. Pat. No. 5,260,291 (Lunt et al.).

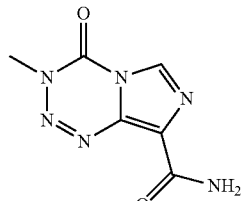

Temozolomide (TMZ)

The therapeutic benefit of temozolomide originates from its ability to alkylate/methylate DNA, which can occur at the N-7 or O-6 positions of guanine residues. This methylation damages DNA and triggers the death of tumor cells. Some tumor cells are able to repair this type of DNA damage and therefore diminish the therapeutic efficacy of temozolomide. The mechanism of this resistance can be by expressing the protein O-6-methylguanine-DNA methyltransferase (MGMT) or O-6-alkylguanine-DNA alkyltransferase (AGT or AGAT). The presence of the O-6-methylguanine-DNA methyltransferase (MGMT) protein in brain tumors predicts poor response to temozolomide and these patients receive little benefit from chemotherapy with temozolomide. Accordingly, new therapies are needed for the treatment of brain tumors and related conditions.

TMZ has been used for the treatment of Grade IV astrocytoma, also known as glioblastoma multiforme, an aggressive brain tumor, as well as oligodendroglioma brain tumors. TMZ has been used for treating melanoma, and is further indicated for relapsed Grade III anaplastic astrocytoma.

While there is clear benefit to anticancer strategies utilizing combinations of drugs that act on different targets, the work described herein demonstrates that dramatic synergy can be observed with compounds that act through disparate mechanisms. This multi-targeting approach can have particular advantages when activation of an enzyme is sought.

PAC-1 is safe in mammals, and a derivative of PAC-1 was efficacious in a phase I clinical trial of pet dogs with lymphoma (Peterson et al., *Cancer Res* 70, 7232-7241 (2010)), thus the observed synergy with TMZ should have significant clinical impact. Interest in activating enzymes with small molecules is increasing rapidly. The data described herein indicate that targeting strategies using PAC-1 and TMZ is a general approach for dramatic enhancement of the intended biologic effect and should have considerable clinical impact due to its efficacy.

Methods of the Invention

The invention provides methods of selectively inducing apoptosis in a cancer cell, comprising administering to a cancer cell a combination of compounds capable of modifying a procaspase-3 molecule of said cancer cell; wherein the combination of compounds is PAC-1 and TMZ. Also provided is a method of selectively inducing apoptosis in a cancer cell, comprising administering to a cancer cell a combination of compounds capable of modifying a procaspase-3 molecule of the cancer cell; wherein the combination of compounds is PAC-1 and TMZ, for example, wherein the cancer cell is in a patient in need of treatment.

The invention provides additional methods where the recited combination of compounds is PAC-1 and TMZ, for example, as a method of treating a cancer cell, comprising (a) identifying a potential susceptibility to treatment of a cancer cell with a procaspase activator compound; and (b) exposing the cancer cell to an effective amount of a combination of a procaspase activator compound and TMZ. Also provided is a method of treating a cancer cell, comprising (a) identifying a potential susceptibility to treatment of a cancer cell with a procaspase activator compound; and (b) exposing said cancer cell to an effective amount of PAC-1 and TMZ; wherein the PAC-1 is capable of activating at least one of procaspase-3 and procaspase-7. Also provided is a method of inducing death in a cancer cell (e.g., killing a cancer cell), comprising administering to a cancer cell TMZ and a compound capable of activating a procaspase-3 molecule of the cancer cell.

The invention further provides a medicament comprising an effective amount of the combination of PAC-1 and TMZ. The medicament can be used in a method of inducing apoptosis in a cell. In some embodiments, the combination of compounds does not cross the blood-brain barrier to as extent that causes appreciable neurotoxic effects in a patient. Methods of the invention include contacting one or more cells with an effective amount of a combination of compounds described herein, in vivo or in vitro. The invention thus also provides methods of treating a cell that include contacting a cell with an effective amount of a combination of compounds described herein.

Definitions

As used herein, the recited terms have the following meanings. All other terms and phrases used in this specification have their ordinary meanings as one of skill in the art would understand. Such ordinary meanings may be obtained by reference to technical dictionaries, such as Hawley's Condensed Chemical Dictionary 14$^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with the recitation of claim elements or use of a "negative" limitation.

The term "and/or" means any one of the items, any combination of the items, or all of the items with which this term is associated. The phrase "one or more" is readily understood by one of skill in the art, particularly when read in context of its usage. For example, one or more substituents on a phenyl ring refers to one to five, or one to four, for example if the phenyl ring is disubstituted.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values, e.g., weight percents, proximate to the recited range that are equivalent in terms of the functionality of the individual ingredient, the composition, or the embodiment.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, as used in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

"Concurrently" means (1) simultaneously in time, or (2) at different times during the course of a common treatment schedule.

"Sequentially" refers to the administration of one active agent used in the method followed by administration of another active agent. After administration of one active agent, the next active agent can be administered substantially immediately after the first, or the next active agent can be administered after an effective time period after the first active agent; the effective time period is the amount of time given for realization of maximum benefit from the administration of the first active agent.

An "effective amount" refers to an amount effective to treat a disease, disorder, and/or condition, or to bring about a recited effect, such as activation or inhibition. For example, an effective amount can be an amount effective to reduce the progression or severity of the condition or symptoms being treated. Determination of a therapeutically effective amount is well within the capacity of persons skilled in the art. The term "effective amount" is intended to include an amount of a compound described herein, or an amount of a combination of compounds described herein, e.g., that is effective to treat or prevent a disease or disorder, or to treat the symptoms of the disease or disorder, in a host. Thus, an "effective amount" generally means an amount that provides the desired effect. In one embodiment, an effective amount refers to an amount of the active agent described herein that are effective, either alone or in combination with a pharmaceutical carrier, upon single- or multiple-dose administration to a cell or a subject, e.g., a patient, at inhibiting the growth or proliferation, inducing the killing, or preventing the growth of hyperproliferative cells. Such growth inhibition or killing can be reflected as a prolongation of the survival of the subject, e.g., a patient beyond that expected in the absence of such treatment, or any improvement in the prognosis of the subject relative to the absence of such treatment.

The terms "treating", "treat" and "treatment" include (i) preventing a disease, pathologic or medical condition from occurring (e.g., prophylaxis); (ii) inhibiting the disease, pathologic or medical condition or arresting its development; (iii) relieving the disease, pathologic or medical condition; and/or (iv) diminishing symptoms associated with the disease, pathologic or medical condition. Thus, the terms "treat", "treatment", and "treating" can extend to prophylaxis and can include prevent, prevention, preventing, lowering, stopping or reversing the progression or severity of the condition or symptoms being treated. As such, the term "treatment" can include medical, therapeutic, and/or prophylactic administration, as appropriate. In some embodiments, the terms "treatment", "treat" or "treated" can refer to (i) prevention of tumor growth or regrowth of the tumor (prophylaxis), (ii) a reduction or elimination of symptoms or the disease of interest (therapy) or (iii) the elimination or destruction of the tumor (cure).

The terms "inhibit", "inhibiting", and "inhibition" refer to the slowing, halting, or reversing the growth or progression of a disease, infection, condition, or group of cells. The inhibition can be greater than about 20%, 40%, 60%, 80%, 90%, 95%, or 99%, for example, compared to the growth or progression that occurs in the absence of the treatment or contacting. Additionally, the terms "induce," "inhibit," "potentiate," "elevate," "increase," "decrease," or the like denote quantitative differences between two states, and can refer to at least statistically significant differences between the two states. For example, "an amount effective to inhibit the growth of hyperproliferative cells" means that the rate of growth of the cells can be, in some embodiments, at least statistically significantly different from the untreated cells. Such terms can be applied herein to, for example, rates of proliferation.

The phrase "inhibiting the growth or proliferation" of the hyperproliferative cell, e.g. neoplastic cell, refers to the slowing, interrupting, arresting, or stopping its growth and metastasis, and does not necessarily indicate a total elimination of the neoplastic growth.

The term "cancer" generally refers to any of a group of more than 100 diseases caused by the uncontrolled growth of abnormal cells. Cancer can take the form of solid tumors and lymphomas, and non-solid cancers such as leukemia. Unlike normal cells, which reproduce until maturation and then only as necessary to replace wounded cells, cancer cells can grow and divide endlessly, crowding out nearby cells and eventually spreading to other parts of the body.

The invention provides methods for treating cancer and cancerous conditions. The term "cancerous condition" relates to any condition where cells are in an abnormal state or condition that is characterized by rapid proliferation or neoplasia. A cancerous condition may be malignant or non-malignant (e.g. precancerous condition) in nature. To farther describe a "cancerous condition", the terms "hyperproliferative", "hyperplastic", "hyperplasia", "malignant", "neoplastic" and "neoplasia" can be used. These terms can be used interchangeably and are meant to include all types of hyperproliferative growth, hyperplastic growth, cancerous growths or oncogenic processes, metastatic tissues or malignantly transformed cells, tissues or organs, irrespective of histopathologic type, stage of invasiveness, or cancerous determination (e.g. malignant and nonmalignant).

The term "neoplasia" refers to new cell growth that results in a loss of responsiveness to normal growth controls, e.g., neoplastic cell growth. A "hyperplasia" refers to cells undergoing an abnormally high rate of growth. However, these terms can be used interchangeably, as their context will reveal, referring generally to cells experiencing abnormal cell growth rates. "Neoplasias" and "hyperplasias" include tumors, which may be either benign, premalignant, carcinoma in-situ, malignant, solid or non-solid.

The combination of PAC-1 and TMZ has been found to be particularly effective for treating cancers of the brain. Cancers of the brain include, but are not limited to, oligodendrogliomas and glioblastomas including glioblastoma multiforme (GBM). Tissues affected by the cancerous cells can be in the brain itself (e.g., the cranium or the central spinal canal) or in lymphatic tissue, in blood vessels, in the cranial nerves, in the brain envelopes (meninges), skull, pituitary gland, or pineal gland. Specific forms of brain cancer that can be treated include astrocytomas, chondromas, chondrosarcomas, chordomas, CNS (central nervous system) lymphomas, craniopharyngiomas, ependymomas, gangliogliomas, ganglioneuromas (also called gangliocytomas), gliomas, including astrocytomas, oligodendrogliomas, and ependymomas, hemangioblastomas (also called vascular tumors), primitive neuroectodermal tumors (PNET) such as medulloblastomas, meningiomas, and vestibular schwannomas (formerly known as acoustic neuroma / schwannoma).

The combination can also be used to treat metastatic tumors that invade the intracranial sphere from cancers originating in other organs of the body. These conditions are typically referred to as secondary brain tumors. Secondary brain tumors that can be treated with the combination of PAC-1 and TMZ include metastatic tumors of the brain that originate from lung cancer, breast cancer, malignant melanoma, kidney cancer, colon cancer, and other carcinomas.

Other examples of cancerous conditions that are within the scope of the invention include, but are not limited to, neuroblastomas and osteogenic carcinomas (e.g. cancer of the bone or neoplastic growth of tissue in bone). Examples of malignant primary bone tumors that can be treated with the combination of PAC-1 and TMZ include osteosarcomas, chondrosarcomas, Ewing's sarcoma, fibrosarcomas, and the like, and secondary bone tumors such as metastatic lesions that have spread from other organs, including carcinomas of the breast, lung, and prostate.

Pharmaceutical Formulations

The compounds described herein can be used to prepare therapeutic pharmaceutical compositions, for example, by combining the compounds with a pharmaceutically acceptable diluent, excipient, or carrier. The compounds may be added to a carrier in the form of a salt or solvate. For example, in cases where compounds are sufficiently basic or acidic to form stable nontoxic acid or base salts, administration of the compounds as salts may be appropriate. Examples of pharmaceutically acceptable salts are organic acid addition salts formed with acids that form a physiological acceptable anion, for example, tosylate, methanesulfonate, acetate, citrate, malonate, tartrate, succinate, benzoate, ascorbate, α-ketoglutarate, and β-glycerophosphate. Suitable inorganic salts may also be formed, including hydrochloride, halide, sulfate, nitrate, bicarbonate, and carbonate salts.

Pharmaceutically acceptable salts may be obtained using standard procedures well known in the art, for example by reacting a sufficiently basic compound such as an amine with a suitable acid to provide a physiologically acceptable ionic compound. Alkali metal (for example, sodium, potassium or lithium) or alkaline earth metal (for example, calcium) salts of carboxylic acids can also be prepared by analogous methods.

The compounds described herein can be formulated as pharmaceutical compositions and administered to a mammalian host, such as a human patient, in a variety of forms. The forms can be specifically adapted to a chosen route of administration, e.g., oral or parenteral administration, by intravenous, intramuscular, topical or subcutaneous routes.

The compounds described herein may be systemically administered in combination with a pharmaceutically acceptable vehicle, such as an inert diluent or an assimilable edible carrier. The solubility of actives can be increase by the use of cyclodextrins, such as 2-hydroxypropyl-β-cyclodextrin. For oral administration, compounds can be enclosed in hard or soft shell gelatin capsules, compressed into tablets, or incorporated directly into the food of a patient's diet. Compounds may also be combined with one or more excipients and used in the form of ingestible tablets, buccal tablets, troches, capsules, elixirs, suspensions, syrups, wafers, and the like. Such compositions and preparations typically contain at least 0.1% of active compound. The percentage of the compositions and preparations can vary and may conveniently be from about 1% to about 60%, or about 2% to about 25%, of the weight of a given unit dosage form. The amount of active compound in such therapeutically useful compositions is such that an effective dosage level can be obtained.

The tablets, troches, pills, capsules, and the like may also contain one or more of the following: binders such as gum tragacanth, acacia, corn starch or gelatin; excipients such as dicalcium phosphate; a disintegrating agent such as corn starch, potato starch, alginic acid and the like; and a lubricant such as magnesium stearate. A sweetening agent such as sucrose, fructose, lactose or aspartame; or a flavoring agent such as peppermint, oil of wintergreen, or cherry flavoring, may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propyl parabens as preservatives, a dye and flavoring such as cherry or orange flavor. Any material used in preparing any unit dosage form should be pharmaceutically acceptable and substantially non-toxic in the amounts employed. In addition, the active compound may be incorporated into sustained-release preparations and devices.

The active compound may be administered intravenously or intraperitoneally by infusion or injection. Solutions of the active compound or its salts can be prepared in water, optionally mixed with a nontoxic surfactant. Dispersions can be prepared in glycerol, liquid polyethylene glycols, triacetin, or mixtures thereof, or in a pharmaceutically acceptable oil. Under ordinary conditions of storage and use, preparations may contain a preservative to prevent the growth of microorganisms.

Pharmaceutical dosage forms suitable for injection or infusion can include sterile aqueous solutions, dispersions, or sterile powders comprising the active ingredient adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions, or by the use of surfactants. The prevention of the action of microorganisms can be brought about by various antibacterial and antifungal agents, for example, parabens, chlorobutanol, phenol, sorbic acid, thiomersal, and the like. In many cases, it will be preferable to include isotonic agents, for example, sugars, buffers, or sodium chloride. Prolonged absorption of the injectable compositions can be brought about by agents delaying absorption, for example, aluminum monostearate and/or gelatin.

Sterile injectable solutions can be prepared by incorporating the active compound in the required amount in the appropriate solvent with various other ingredients enumerated above, as required, optionally followed by filter sterilization. In the case of sterile powders for the preparation of sterile injectable solutions, methods of preparation can include vacuum drying and freeze drying techniques, which yield a powder of the active ingredient plus any additional desired ingredient present in the previously sterile-filtered solutions.

Useful dosages of the compounds described herein can be determined by comparing their in vitro activity, and in vivo activity in animal models. Methods for the extrapolation of effective dosages in mice, and other animals, to humans are known to the art; for example, see U.S. Pat. No. 4,938,949 (Borch et al.). The amount of a compound, or an active salt or derivative thereof, required for use in treatment will vary not only with the particular compound or salt selected but also with the route of administration, the nature of the condition being treated, and the age and condition of the patient, and will be ultimately at the discretion of an attendant physician or clinician.

The combination of compounds can be conveniently administered in a unit dosage form, for example, containing 100 to 5,000 mg/m$^2$, 300 to 4,000 mg/m$^2$, 370 to 3,700 mg/m$^2$, 50 to 750 mg/m$^2$, or 750 to 4,000 mg/m$^2$ of active ingredient per unit dosage form. Each compound, individually or in combination, can also be administered at about 1 mg/kg to about 250 mg/kg, about 10 mg/kg to about 100 mg/kg, about 10 mg/kg to about 50 mg/kg, about 50 mg/kg to about 100 mg/kg, about 10 mg/kg to about 50 mg/kg, or about 10 mg/kg, about 25 mg/kg, about 50 mg/kg, about 75 mg/kg, about 100 mg/kg, or about 150 mg/kg, or a range from any one of the aforementioned values to any other of the aforementioned values. The compounds can also be administered to a subject to provide a steady-state plasma concentration of the drugs, alone or in combination, of about 1 μmol/L to about 25 μmol/L, or about 10 μmol/L, or about 15 μmol/L.

In some embodiments, the invention provides the compounds in effective concentrations at about 10 nM to about 100 μM. In another embodiment, the effective concentrations are from about 200 nM to about 50 μM, about 500 nM to about 40 µM, about 750 nM to about 25 µM, about 1 µM to about 20 µM, or about 1 µM to about 10 µM. In another embodiment, the effective concentration is considered to be a value such as a 50% activity concentration in a direct procaspase activation assay, in a cell apoptosis induction assay, or in an animal clinical therapeutic assessment. In one embodiment, such value is less than about 200 µM. In another embodiment, the value is less than about 10 µM but greater than about 10 nM. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The compounds described herein can be effective antitumor agents and have higher potency and/or reduced toxicity as compared to the administration of any single agent. The invention provides therapeutic methods of treating cancer in a mammal, which involve administering to a mammal having cancer an effective amount of a compound or composition described herein. A mammal includes a primate, human, rodent, canine, feline, bovine, ovine, equine, swine, caprine, bovine and the like. Cancer refers to any various type of malignant neoplasm, for example, colon cancer, breast cancer, melanoma and leukemia, among others described herein, and in general is characterized by an undesirable cellular proliferation, e.g., unregulated growth, lack of differentiation, local tissue invasion, and metastasis.

The ability of a compound of the invention to treat cancer may be determined by using assays well known to the art. For example, the design of treatment protocols, toxicity evaluation, data analysis, quantification of tumor cell kill, and the biological significance of the use of transplantable tumor screens are known. In addition, ability of a compound to treat cancer may be determined using the assays described above and in the citations and patent documents cited herein.

The invention also provides prodrug forms of compounds. Any compound that will be converted in vivo to provide PAC-1 or TMZ is a prodrug. Numerous methods of forming prodrugs are well known in the art. Examples of prodrugs and methods of preparing them are found, inter alia, in Design of Prodrugs, edited by H. Bundgaard, (Elsevier, 1985), Methods in Enzymology, Vol. 42, at pp. 309-396, edited by K. Widder, et. al. (Academic Press, 1985); A Textbook of Drug Design and Development, edited by Krosgaard-Larsen and H. Bundgaard, Chapter 5, "Design and Application of Prodrugs," by H. Bundgaard, at pp. 113-191, 1991); H. Bundgaard, Advanced Drug Delivery Reviews, Vol. 8, p. 1-38 (1992); H. Bundgaard, et al., *Journal of Pharmaceutical Sciences*, Vol. 77, p. 285 (1988); and Nogrady (1985) Medicinal Chemistry A Biochemical Approach, Oxford University Press, New York, pages 388-392).

Additionally, in some embodiments, PAC-1 can be exchanged for a PAC-1 derivative or other inhibitor, such as a compound described in U.S. Pat. No. 7,632,972 (Hergenrother et al.), U.S. Patent Publication Nos. 2012/0040995 (Hergenrother et al.) and 2007/0049602 (Hergenrother et al.), and U.S. application Ser. No. 12/597,287 (Hergenrother et al.). Useful compounds, methods, and techniques for cancer therapy that can be used in combination with the disclosure herein are described in the aforementioned documents, as well as in U.S. Pat. No. 6,303,329 (Heinrikson et al.), U.S. Pat. No. 6,403,765 (Alnemri), U.S. Pat. No. 6,878,743 (Choong et al.), and U.S. Pat. No. 7,041,784 (Wang et al.), and U.S. Patent Publication No. 2004/0180828 (Shi). Methods for performing the tests and evaluating cancer cell lines can be carried out as described by Putt et al., *Nature Chemical Biology* 2006, 2(10), 543-550; Peterson et al., *J. Mol. Biol.* 2009, 388, 144-158; and Peterson et al., *Cancer Res.* 2010, 70(18), 7232-7241.

The following Example is intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1

In vivo Efficacy of PAC-1 in Combination with Temozolomide (TMZ) in 9 L Rat Glioma 9 L gliosarcoma was maintained as a solid subcutaneous mass in the flanks of F344 rats. For intracranial implantation, the 9 L gliosarcoma tumor was surgically excised from the carrier animal and sliced into 1 mm$^3$ pieces at the time of implantation. These 1 mm$^3$ tumor pieces were intracranially implanted in 32 F344 rats as described previously (Joshi et al., *Evaluation of tyrosine kinase inhibitor combinations for glioblastoma therapy*. PLoS One (2012) 7: e44372; Gallia et al., *Inhibition of Akt inhibits growth of glioblastoma and glioblastoma stem-like cells*. Mol. Cancer Ther. (2009) 8: 386-393).

The animals were divided into the following four experimental groups with eight animals per group: (1) Control, (2) PAC-1 alone, (3) TMZ alone, and (4) PAC -1+TMZ. The control animals only received water. Two groups of animals from PAC-1 alone and PAC-1+TMZ received an oral gavage of PAC-1 suspended in water starting day 0 six hours post implantation. PAC-1 was administered only for 5 days from day 0 to day 4. The animals from TMZ alone and PAC -1+TMZ groups received 5 doses of TMZ in water administered orally from day 5 to day 9. The experimental animals did not receive any treatment thereafter and were evaluated for overall survival. The PAC-1+TMZ combination treated animals had a significantly increased survival (median survival=28 days) compared to animals treated with TMZ alone (median survival=20 days) or untreated control animals (median survival=20 days) (FIG. 1).

Example 2

Pharmaceutical Dosage Forms

The following formulations illustrate representative pharmaceutical dosage forms that may be used for the therapeutic or prophylactic administration of the combination compounds described herein (e.g., PAC-1 and TMZ), or pharmaceutically acceptable salts or solvates thereof (hereinafter referred to as 'Compounds X'):

| (i) Tablet 1 | mg/tablet |
|---|---|
| 'Compounds X' | 200.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 400.0 |

-continued

| (ii) Tablet 2 | mg/tablet |
|---|---|
| 'Compounds X' | 120.0 |
| Microcrystalline cellulose | 410.0 |
| Starch | 50.0 |
| Sodium starch glycolate | 15.0 |
| Magnesium stearate | 5.0 |
|  | 600.0 |

| (iii) Capsule | mg/capsule |
|---|---|
| 'Compounds X' | 110.0 |
| Colloidal silicon dioxide | 1.5 |
| Lactose | 465.5 |
| Pregelatinized starch | 120.0 |
| Magnesium stearate | 3.0 |
|  | 700.0 |

| (iv) Injection 1 (1 mg/mL) | mg/mL |
|---|---|
| 'Compounds X' | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/mL) | mg/mL |
|---|---|
| 'Compounds X' | 10.0 |
| Monobasic sodium phosphate | 0.3 |
| Dibasic sodium phosphate | 1.1 |
| Polyethylene glycol 400 | 200.0 |
| 0.1N Sodium hydroxide solution (pH adjustment to 7.0-7.5) | q.s. |
| Water for injection | q.s. ad 1 mL |

| (vi) Aerosol | mg/can |
|---|---|
| 'Compounds X' | 20 |
| Oleic acid | 10 |
| Trichloromonofluoromethane | 5,000 |
| Dichlorodifluoromethane | 10,000 |
| Dichlorotetrafluoroethane | 5,000 |

These formulations may be prepared by conventional procedures well known in the pharmaceutical art. It will be appreciated that the above pharmaceutical compositions may be varied according to well-known pharmaceutical techniques to accommodate differing amounts and types of active ingredient 'Compounds X'. Aerosol formulation (vi) may be used in conjunction with a standard, metered dose aerosol dispenser. Additionally, the specific ingredients and proportions are for illustrative purposes. Ingredients may be exchanged for suitable equivalents and proportions may be varied, according to the desired properties of the dosage form of interest.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A composition comprising:
(a) a compound of Formula (I):

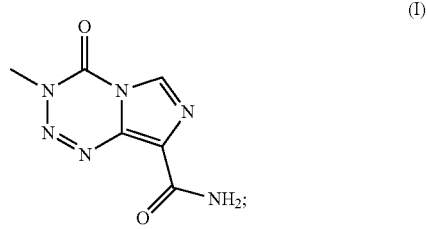

(b) the compound PAC-1:

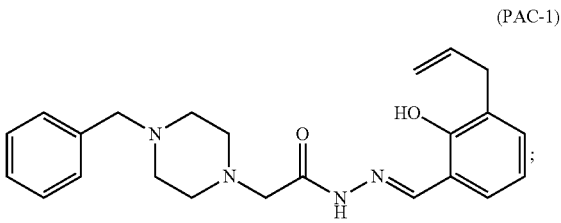 [SMILES: C=CCc1cccc(/C=N/NC(=O)CN2CCN(Cc3ccccc3)CC2)c1O]

and
(c) a pharmaceutically acceptable diluent, excipient, or carrier;
wherein the concentration of the compound of Formula I is about 250 μM to about 750 μM and the concentration of PAC-1 is about 5 μM to about 30 μM, wherein about means a variation of 20% of the concentration.

2. The composition of claim 1 wherein the carrier comprises water and optionally a buffer, a cyclodextrin, or a combination thereof.

3. The composition of claim 2 wherein the cyclodextrin is present and is 2-hydroxypropyl-β-cyclodextrin.

4. The composition of claim 1 wherein the concentration of the compound of Formula I is about 250 μM, about 500 μM, or about 750 μM.

5. The composition of claim 1 wherein the concentration of PAC-1 is about 5 μM, about 10 μM, about 12.5 μM, or about 25 μM.

6. A method of inhibiting the growth or proliferation of cancer cells in a cancer selected from the group comprising contacting cancer cells with an effective amount of a composition of claim 1, thereby inhibiting the growth or proliferation of the cancer cells, wherein the cancer is selected from the group consisting of cancer of the brain and cancer of bone.

7. The method of claim 6 wherein the cancer cells are glioblastoma cells or oligodendroglioma cells.

8. The method of claim 6 wherein the cancer cells are osteosarcoma cells.

9. A method of inducing apoptosis in a cancer cell comprising contacting the cancer cell with an effective amount of a compound of Formula (I):

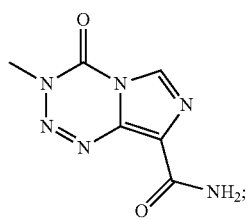

(I)

and an effective amount of the compound PAC-1:

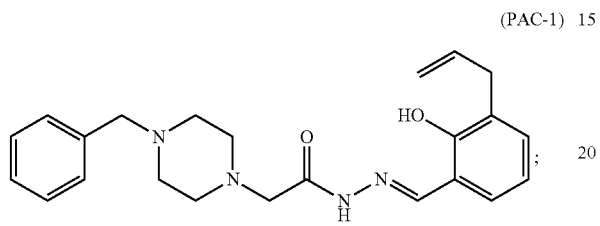

(PAC-1)

wherein apoptosis is thereby induced in the cancer cell, wherein the concentration of the compound of Formula I is about 250 μM to about 750 μM and the concentration of PAC-1 is about 5 μM to about 30 μM, wherein about means a variation of 20% of the concentration, and wherein the cancer is selected from the group consisting of cancer of the brain and cancer of bone.

10. The method of claim 9 wherein the contacting is in vitro.

11. The method of claim 9 wherein the contacting is in vivo.

12. The method of claim 9 wherein the cancer cell is contacted with the compound of Formula (I) and the PAC-1 concurrently.

13. The method of claim 9 wherein the cancer cell is contacted with the compound of Formula (I) prior to contacting the cancer cell with PAC-1.

14. The method of claim 9 wherein the cancer cell is contacted with PAC-1 prior to contacting the cancer cell with the compound of Formula (I).

15. A method of treating a cancer in a patient in need thereof comprising administering to a patient, concurrently or sequentially, a therapeutically effective amount of a compound of Formula (I):

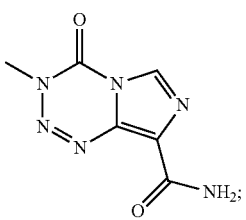

(I)

and an effective amount of the compound PAC-1:

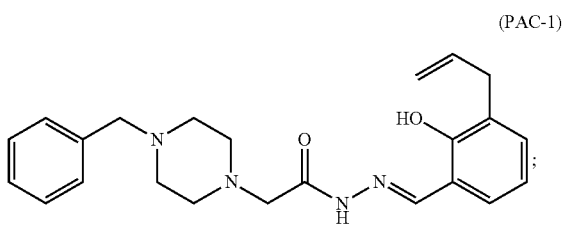 [SMILES: C=CCc1cccc(/C=N/NC(=O)CN2CCN(Cc3ccccc3)CC2)c1O]

(PAC-1)

wherein the cancer is thereby treated, wherein the concentration of the compound of Formula I is about 250 μM to about 750 μM and the concentration of PAC-1 is about 5 μM to about 30 μM, wherein about means a variation of 20% of the concentration, and wherein the cancer is selected from the group consisting of cancer of the brain and cancer of bone.

16. The method of claim 15 wherein the compound of Formula (I) and the compound PAC-1 are administered concurrently.

17. The method of claim 15 wherein the compound of Formula (I) and the compound PAC-1 are administered sequentially.

18. The method of claim 17 wherein the compound of Formula (I) is administered before the compound PAC-1.

19. The method of claim 17 wherein the compound of Formula (I) is administered after the compound PAC-1.

20. The composition of claim 1 wherein the concentration of the compound of Formula I is about 250 μM, about 500 μM, or about 750 μM, and the concentration of PAC-1 is about 5 μM, about 10 μM, about 12.5 μM, or about 25 μM.

* * * * *